United States Patent
Kamijo et al.

(10) Patent No.: US 6,881,962 B2
(45) Date of Patent: Apr. 19, 2005

(54) PAPER FLUORESCENCE DETECTION SENSOR

(75) Inventors: Hideaki Kamijo, Tokyo (JP); Kouyou Usami, Tokyo (JP)

(73) Assignee: Nidec Copal Corporation, Tokyo (JP)

( * ) Notice: Subject to any disclaimer, the term of this patent is extended or adjusted under 35 U.S.C. 154(b) by 166 days.

(21) Appl. No.: 10/176,628

(22) Filed: Jun. 24, 2002

(65) Prior Publication Data

US 2002/0195571 A1 Dec. 26, 2002

(30) Foreign Application Priority Data

Jun. 25, 2001 (JP) ...................................... P2001-191708

(51) Int. Cl.$^7$ ............................................... G01N 21/64
(52) U.S. Cl. ...................................... 250/458.1; 380/54
(58) Field of Search .......................... 250/458.1; 380/54

(56) References Cited

U.S. PATENT DOCUMENTS

| | | |
|---|---|---|
| 5,640,463 A | 6/1997 | Csulits |
| 5,918,960 A | 7/1999 | Hopwood et al. |
| 2003/0039359 A1 * | 2/2003 | Thierauf ........................ 380/54 |

FOREIGN PATENT DOCUMENTS

| | | |
|---|---|---|
| DE | 19958048 A1 * | 6/2001 |
| WO | WO 95/19019 | 7/1995 |

* cited by examiner

*Primary Examiner*—Constantine Hannaher
*Assistant Examiner*—Shun Lee
(74) *Attorney, Agent, or Firm*—Leydig, Voit & Mayer, Ltd.

(57) ABSTRACT

In the accurate inspection of a paper sheet (for example, the type and authenticity of banknotes) light incident on the paper sheet that is being transported is controlled to be constant. To achieve such control, in accordance with the present invention, an illumination monitor is disposed facing an illumination window, and the light reflected by an inner surface of the illumination window is detected by the illumination monitor. Since, in this configuration, the illumination monitor faces the illumination window, the illumination monitor has a monitor region on a transportation path. The illumination monitor is directed toward the illumination window so that the monitor region is positioned outside an illumination region formed by a light-emitting element, thereby preventing the illumination monitor from picking up the light reflected from a transportation path of the paper sheet.

4 Claims, 3 Drawing Sheets

PAPER FLUORESCENCE DETECTION SENSOR

BACKGROUND OF THE INVENTION

1. Field of the Invention

The present invention relates to a paper fluorescence detection sensor used for judging the type or authenticity of paper such as banknotes and the like.

2. Description of the Related Art

The conventional technology of this technological field is described in Japan Patent Kouhyou No. Hei9-507326 (WO95/19019). In the apparatus described in this open publication, a banknote is illuminated with UV radiation, the level of UV light reflected by the banknote is measured by a first photocell, at the same time the intensity of fluorescence generated on the banknote is measured by a second photocell, and the authenticity of the banknote is determined based on both results of measurement by the first and second photocell.

However, the following problems are associated with the above-described conventional apparatus. That is, the intensity of UY radiation illuminating the banknote tends to be unstable at the initial stage when the light source is turned on, and often fluctuates due to voltage fluctuations or degradation over time. As a result, the authenticity of banknotes and the like may not be detected accurately.

SUMMARY OF THE INVENTION

The present invention was developed to resolve the above-described problems, and it is an object of the present invention to provide a paper fluorescence detection sensor capable of appropriately monitoring the intensity of light emitted by a light-emitting element (light source), thereby keeping the light-emitting element radiating light stably.

Thus, the present invention provides a paper fluorescence detection sensor in which paper sheets are illuminated with light as the paper sheets are being transported, and fluorescent light generated on the surface of the paper sheets is detected, this sensor comprising: a light-emitting element which is housed in a case and which forms an illumination region on a transportation path of the paper sheets by emitting light toward the transportation path via an illumination window; a light-receiving element housed in the case, which receives fluorescent light generated from the surface of the paper sheets via a light-receiving window; and an illumination monitor disposed inside the case so as to face the illumination window, which receives the light of the light-emitting element reflected by the inner surface of the illumination window, and which has a monitor region positioned outside the illumination region on the transportation path.

The present invention will become more fully understood from the detailed description given hereinbelow and the accompanying drawings which are given by way of illustration only, and thus are not to be considered as limiting the present invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DESCRIPTION OF THE PREFERRED EMBODIMENTS

A preferred embodiment of the paper fluorescence detection sensor in accordance with the present invention will be described below in reference to the appended drawings.

Figure 1:
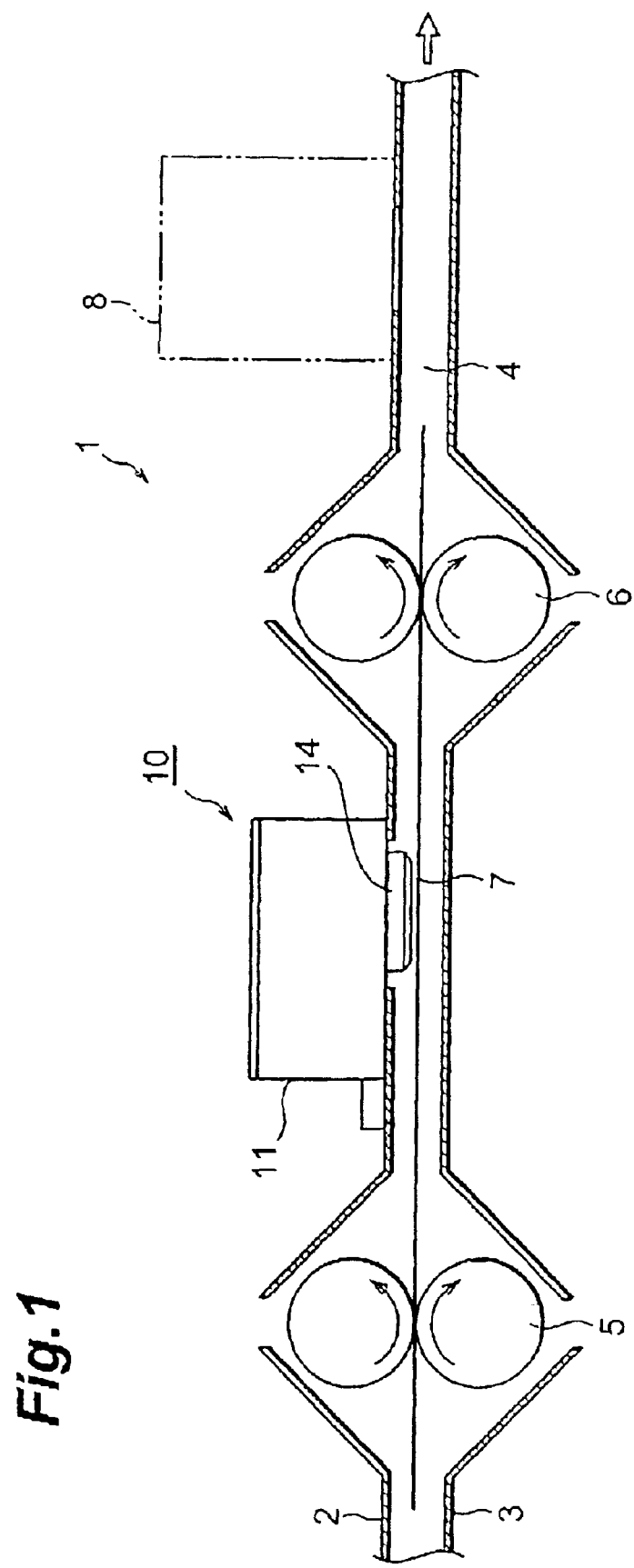
FIG. 1 is a cross-sectional view illustrating an example of a paper inspection device employing the paper fluorescence detection sensor in accordance with the present invention.

FIG. 1 is a cross-sectional view illustrating a paper inspection device 1. The object of inspection by the paper inspection device 1 is to discriminate between forged banknotes obtained by color copying and genuine banknotes. Forged banknotes obtained by color copying contain a large amount of fluorescence components. The paper inspection device 1 detects forged banknotes using such feature of forged banknotes.

The paper inspection device 1 comprises a linear transportation path 4 disposed between the upper and lower guide plates 2, 3. Transportation rollers 5, 6 move the transportation path 4, and a banknote 7 placed on the transportation path 4 is reliably transported toward the exit side. A banknote recognition device 8 for distinguishing the denomination is disposed at a downstream point of the transportation path 4.

The banknote recognition device 8 has a structure, which is not shown in the figure, such that the surface of banknote 7 is illuminated by a light source such as an LED and the light reflected from the banknote 7 is collected by a CCD camera. An image captured by the CCD camera is compared with known image data and the denomination of the banknote is discerned. However, recent improvements in the accuracy of color copying have made it difficult to authenticate the banknote 7 by image recognition alone.

Figure 2:
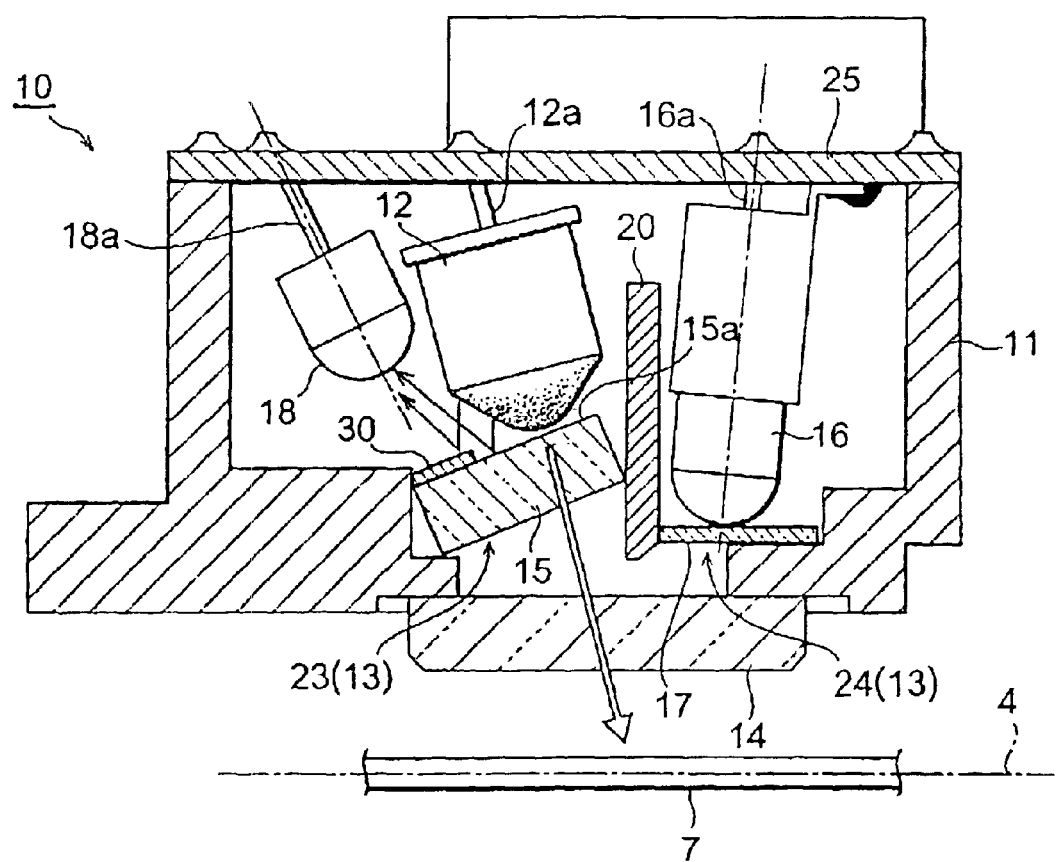
FIG. 2 is a cross-sectional view illustrating an embodiment of the paper fluorescence detection sensor in accordance with the present invention.

Accordingly, a paper fluorescence detection sensor 10 is disposed upstream of the banknote recognition device 8. The paper fluorescence detection sensor 10, as shown in FIG. 2, comprises a partition 20, which divides the inner space of a case 11 in substantially rectangular parallelepiped shape along the longitudinal direction into the space where a light-emitting element (UV LED) 12 is accommodated and the space where a light-receiving element 16 is accommodated. The partition 20 divides a window 13 of the case 11 into a first window 23 (composed of the below-described illumination window 15) and a second window 24 (composed of the below-described light-receiving window 17). The UV LED 12 which emits light toward the transportation path 4 of banknote 7 is housed in one of the spaces formed by the partition 20 in the case 11. This UV LED 12 is fixed to a drive circuit substrate 25 of the case 11 via a lead 12a.

The light-emitting element 12 used herein is a UV LED with a visible light component included in the radiation. LED is used as a light source because it occupies small space, thereby contributing to downsizing the case 11. Therefore, LED is most appropriate for this paper fluorescence detection sensor 10, which has been designed with consideration for size reduction. Further, LED has an advantage in that the brightness spread is limited, and fluctuation in brightness intensity over time is small.

A dustproof glass plate 14 is fixed with an adhesive or the like to the lower part of the case 11 so as to close the opening of the case 11. A quartz glass with very high UV transmittance is used for the dustproof glass plate 14.

Furthermore, in the space of the UV LED 12 side, the illumination window 15 composed of a UV-transmitting filter is fixed slanted with an adhesive or the like to the case 11 and the partition 20 inside of the dustproof glass plate 14. Therefore, because light emitted from the UV LED 12 passes through the UV-transmitting filter 15, the UV component (for example, with a wavelength of around 300–400 nm) is released onto the transportation path 4 via the illumination window 15 and the dust proof glass plate 14. The banknote 7 passing directly beneath the dust proof glass plate 14 on the transportation pass 4 is illuminated with UV light.

A light-receiving element (photosensor) 16 for detecting the fluorescence emitted from the surface of banknote 7 is housed in the other space formed by the partition 20 inside the case 11. This light-receiving element 16 is fixed to the drive circuit substrate 25 of case 11 via a lead 16a. Therefore, when the banknote 7 illuminated with UV light contains a fluorescent component, the excited fluorescence is emitted from the banknote 7 and detected by the light-receiving element 16. For example, when a forged banknote 7 obtained by color copying is illuminated with UV light, since paper for color copying contains a large amount of fluorescent components, the intensity of fluorescence detected by the light-receiving element 16 is high. By contrast, a genuine banknote contains practically no fluorescent components and the intensity of fluorescence detected by the light-receiving element 16 is very small.

The light-receiving window 17 composed of a UV-cut filter is fixed with an adhesive to the case 11 and the partition 20 inside of the dust proof glass plate 14 so as to cover the opening of the space where the light-receiving element 16 is accommodated. Such a UV-cut filter is used for the following reason: the light reflected by the surface of banknote 7 contains a UV component and this UV component has a high energy characteristic. Therefore, the UV component must be removed to avoid erroneous detection.

Accurate inspection of a banknote (for example, type and authenticity of banknote) is impossible unless the intensity of light illuminating the banknote 7 on the transportation path 4 is controlled in a constant state. Therefore, the intensity of light emitted by the UV LED 12 has to be adjusted with an illumination monitor 18 measuring the intensity of light emitted by the UV LED 12. However, the intensity of light detected by the illumination monitor 18 is affected by the following external factors (factors other than changes in the intensity of light emitted by the UV LED 12) such that accurate measurement of the intensity of light emitted by the UV LED 12 with the illumination monitor 18 maybe impeded. Banknotes 7 are successively transported at a high speed and at a constant spacing on the transportation pass 4, and the UV LED 12 constantly illuminates either the banknotes 7 or the portion where no banknote 7 is present (between the banknote 7 and the next banknote 7). Namely, in one occasion the light reflected by the banknote 7 is incident from the illumination window 15, and in the other occasion no reflected light from the banknote 7 is generated. As a result, the intensity of light incident on the illumination window 15 changes intermittently. Furthermore, the intensity of reflected light differs depending on the type of banknote 7 (for example, a 1000-yen banknote or a 10,000-yen banknote). That is, the intensity of light incident on the illumination window 15 changes each time the banknote denomination is changed. Such changes in the intensity of light incident on the illumination window 15 from outside case 11 may fluctuate the intensity of light detected by the illumination monitor 18.

Figure 3:
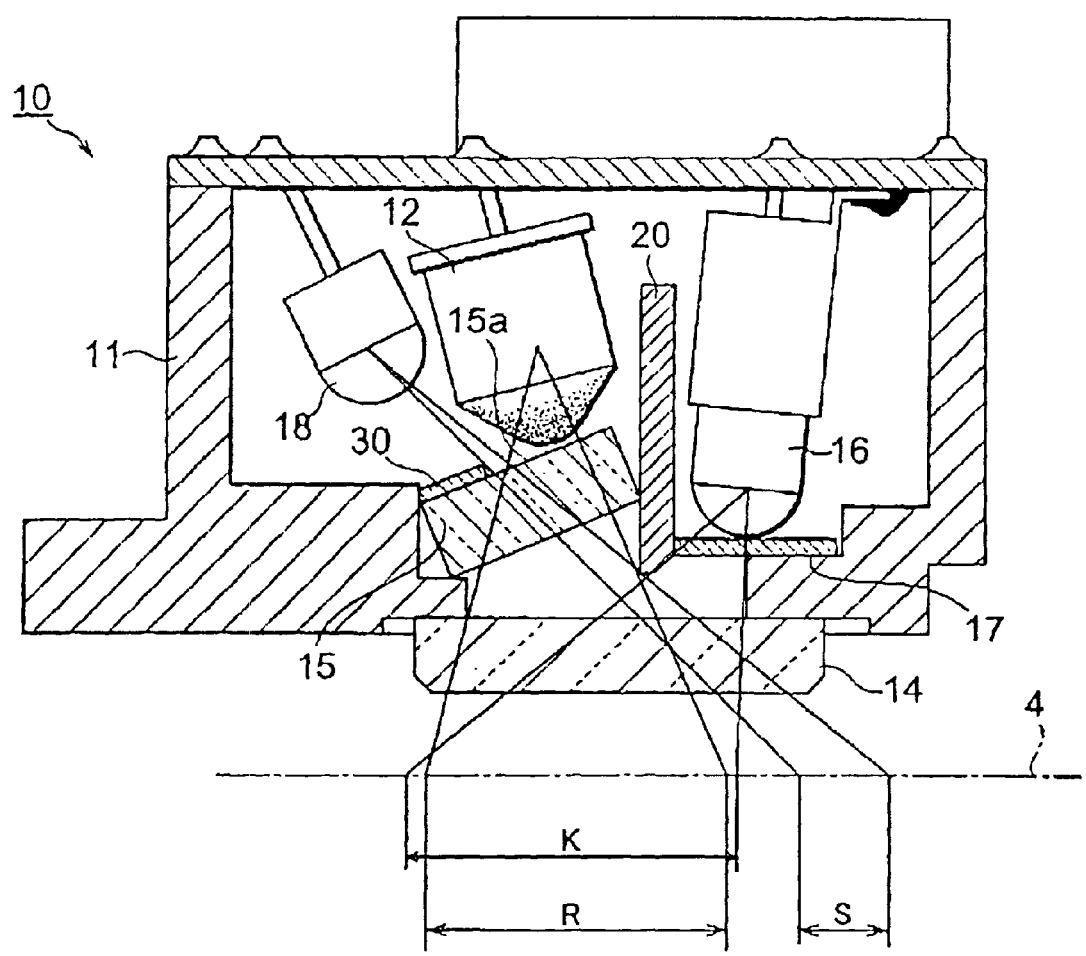
FIG. 3 is a cross-sectional view of the paper fluorescence detection sensor shown in FIG. 2, showing an illumination region R, a monitor region S and a light reception region K.

In order to accurately monitor the changes in the intensity of light of the UV LED 12, the illumination monitor 18 composed of a photosensor is disposed in the space of the UV LED 12 side. In order to receive the light reflected from the inner surface 15a of illumination window 15, the illumination monitor 18 is disposed inside the case 11 so as to face the inner surface 15a of the illumination window 15 and is fixed to the drive circuit substrate 25 via the lead 18a. Furthermore, as shown in FIG. 3, the illumination monitor 18 forms a monitor region S on the transportation path 4, outside the illumination region R created by the UV LED 12, so as to eliminate as thoroughly as possible the effect of light reflected from the transportation pass 4.

The illumination region R and monitor region S of the, present embodiment will be described hereinbelow. The illumination region R is a portion from which the UV light emitted by the UV LED 12 via the illumination window 15 is reflected, that is, the region on the transportation path 4 which is illuminated with the UV light from the UV LED 12. The monitor region S is the region on the transportation path 4 from which the scattered light or reflected light can enter the illumination monitor 18.

Specifically, in forming the monitor region S in such a position, a conventional light-receiving element with a comparatively wide light reception region is used as the illumination monitor 18 with the aim of reducing the production cost. An aluminum light-shielding sheet 30, as an example of light-shielding means, is fixed with an adhesive to the inner surface 15a of illumination window 15 composed of a UV-transmitting filter. This light-shielding sheet 30 restricts the inner side of the monitor region S so that the illumination region R does not enter the monitor region S on the transportation path 4. Further, the outer side of the monitor region S is restricted by the lower end of partition 20. In this manner, while causing the light from the UV LED 12 to pass through the UV-transmitting filter, and at the same time causing the light to be reflected by the inner surface 15a of the UV-transmitting filter, the illumination monitor 18 is prevented from picking up the light reflected from the illumination region R (reflected light on the transportation path 4), whereby the effect of external factors (factors other than changes in the intensity of light emitted by the UV LED 12) on the intensity of light detected by the illumination monitor 11 is eliminated as thoroughly as possible.

Thus, the monitor region S is positioned outside the illumination region R, enabling the illumination monitor 18 appropriately monitor the intensity of light emitted from the UV LED 12 by detecting the light reflected from the inner surface 15a of the illumination window 15.

Furthermore, by employing a structure in which the illumination window 15 is provided with light-shielding means while restricting the light-receiving region of the illumination monitor 18, the use of conventional inexpensive light-receiving elements with wide light-receiving region becomes possible.

Moreover, since a structure is used in which the light-shielding sheet 30 is employed as light-shielding means and the light-shielding sheet 30 is fixed to the inner surface 15a of illumination window 15, the monitor region S can be limited to an arbitrary size by a simple operation of attaching (for example, with an adhesive) a light shielding sheet molded as a separate component, that is, with out producing the light-shielding means integrally with the illumination window, to the inner surface 15a of illumination window 15. This facilitates arbitrary setting of the monitor region S and also facilitates fine tuning of the monitor region S during manufacture.

A structure in which the light-shielding sheet 30 is formed from a reflective material such as aluminum increases the intensity of light reflected from the inner surface 15a of illumination window 15, because the illumination monitor 18 receives not only the light reflected by the inner surface 15a of the illumination window 15, but also the intensive light reflected by the light-shielding sheet 30. As a result, the intensity of light received by the illumination monitor is increased and fluctuations in the intensity of light emitted by the light-emitting element can be accurately detected, thereby keeping the UV LED 12 emitting light stably.

In FIG. 3, the reference symbol K denotes the light-receiving region of light-receiving element 16 on the transportation pass 4, and this light-receiving region K is slightly larger than the illumination region R.

The present invention is not limited to the above-described embodiment. For example, light-shielding means may be embedded in the illumination window 15, or light-shielding means maybe formed from a light-absorbing material, rather than reflective material.

From the invention thus described, it will be obvious that the embodiments of the invention may be varied in many ways. Such variations are not to be regarded as a departure from the spirit and scope of the invention, and all such modifications as would be obvious to one skilled in the art are intended for inclusion within the scope of the following claims.

What is claimed is:

1. A paper fluorescence detection sensor which detects fluorescent light generated from paper sheets by illuminating the paper sheets with light as the paper sheets are being transported, comprising:

a case;

a light-emitting element which is housed in said case, and which forms an illumination region on a transportation path of paper sheets by emitting light toward the transportation path via an illumination window, said light-emitting element facing an inner surface of said illumination window;

a light-detecting element which is housed in said case, and which detects fluorescent light generated by the paper sheets, via a detection window;

light-shielding means attached to only a part of said illumination window and opaque to the light emitted by said light-emitting element; and an illumination monitor disposed in said case facing said inner surface of said illumination window, which detects the light emitted by said light-emitting element and reflected by said inner surface of said illumination window, said illumination monitor monitoring light in a monitor region that is outside the illumination region on the transportation path, the light-shielding means limiting extent of the monitor region whereby variations in intensity of the light emitted by said light-emitting element are accurately detected.

2. The paper fluorescence detection sensor according to claim 1, wherein said light-shielding means is embedded in said illumination window, restricting the monitor region.

3. The paper fluorescence detection sensor according to claim 1, wherein said light-shielding means includes a light-shielding sheet fixed to said inner surface of said illumination window.

4. The paper fluorescence detection sensor according to claim 1, wherein said light-shielding means includes a reflective material reflecting light emitted by said light-emitting element.

* * * * *